United States Patent
Rubin et al.

(10) Patent No.: US 11,213,766 B1
(45) Date of Patent: Jan. 4, 2022

(54) SYSTEMS AND METHODS FOR REHABILITATING ALCOHOL

(71) Applicants: Matthew Rubin, Indianapolis, IN (US); Adam Daniel Ambrecht, Kennesaw, GA (US); Jessica Clare Halstead, Indianapolis, IN (US)

(72) Inventors: Matthew Rubin, Indianapolis, IN (US); Adam Daniel Ambrecht, Kennesaw, GA (US); Jessica Clare Halstead, Indianapolis, IN (US)

(*) Notice: Subject to any disclaimer, the term of this patent is extended or adjusted under 35 U.S.C. 154(b) by 0 days.

(21) Appl. No.: 16/939,340

(22) Filed: Jul. 27, 2020

(51) Int. Cl.
| | |
|---|---|
| *B01D 3/10* | (2006.01) |
| *C07C 29/84* | (2006.01) |
| *B01D 3/42* | (2006.01) |
| *C12G 3/08* | (2006.01) |
| *C12F 3/06* | (2006.01) |
| *B01D 3/00* | (2006.01) |

(52) U.S. Cl.
CPC ............ *B01D 3/106* (2013.01); *B01D 3/001* (2013.01); *B01D 3/42* (2013.01); *C07C 29/84* (2013.01); *C12F 3/06* (2013.01); *C12G 3/08* (2013.01)

(58) Field of Classification Search
CPC .............. C07C 29/84; C12F 3/06; C12G 3/08
See application file for complete search history.

(56) References Cited

U.S. PATENT DOCUMENTS

| | | | | |
|---|---|---|---|---|
| 4,347,321 | A * | 8/1982 | Lionelle | B01D 3/001 |
| | | | | 435/161 |
| 5,458,739 | A * | 10/1995 | Boucher | C12H 6/02 |
| | | | | 202/153 |
| 6,019,034 | A * | 2/2000 | Ford, Sr. | C12H 1/16 |
| | | | | 141/65 |
| 6,626,092 | B2 * | 9/2003 | Tarlow | A23G 9/28 |
| | | | | 220/231 |
| 9,200,243 | B2 | 12/2015 | Mosier et al. | |
| 10,428,298 | B1 * | 10/2019 | Salzman | B01D 3/10 |
| 2013/0243922 | A1 * | 9/2013 | Lynn | A23L 2/46 |
| | | | | 426/494 |

\* cited by examiner

*Primary Examiner* — Jonathan Miller
(74) *Attorney, Agent, or Firm* — C. John Brannon; Brannon Sowers & Cracraft PC

(57) ABSTRACT

A method for rehabilitating alcohol, including placing a quantity of ethanol solution in a pressure-controllable environment, decreasing the pressure of the pressure-controllable environment to about 25 Torr, holding the pressure of the pressure-controllable environment at about 25 Torr for a first predetermined period of time, removing unwanted congeners, such as ethyl acetate, from the ethanol solution to yield a treated ethanol solution, and removing treated solution from the pressure-controllable environment.

13 Claims, 16 Drawing Sheets

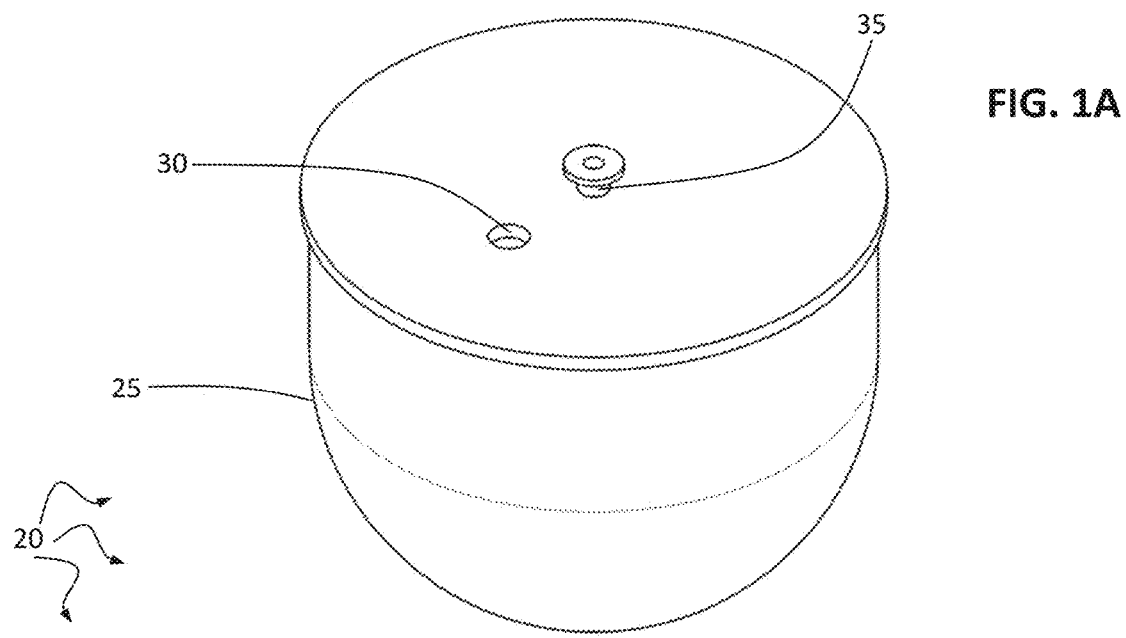
FIG. 1A
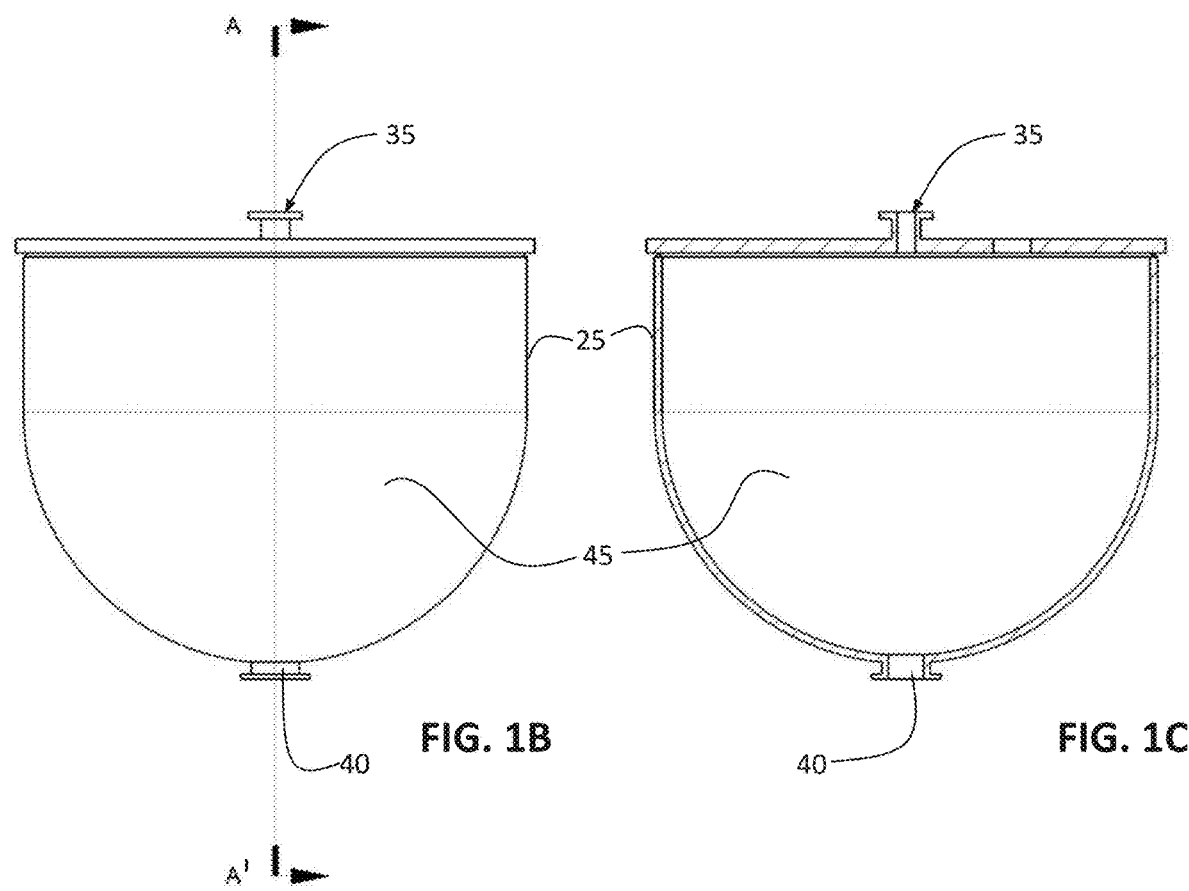
FIG. 1B
FIG. 1C
Section A-A'

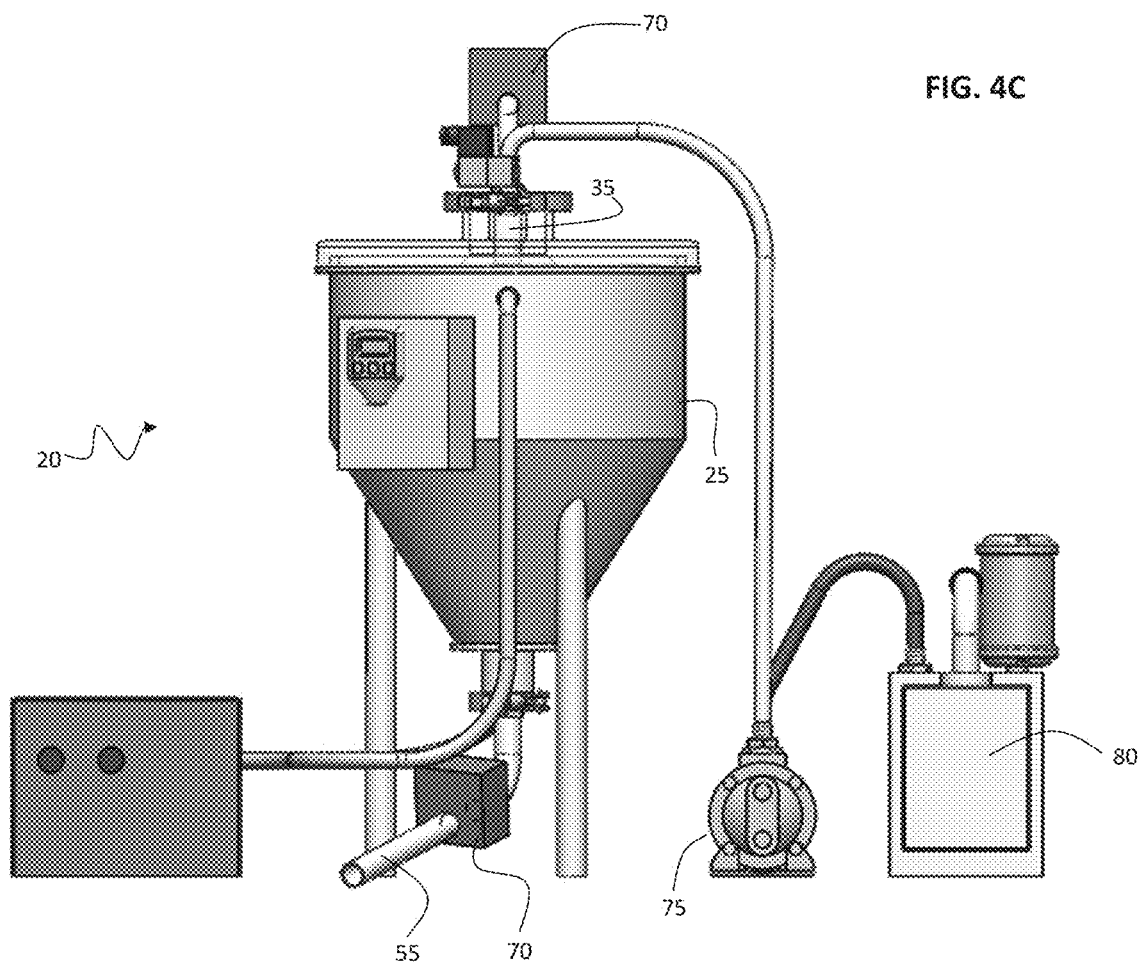

SYSTEMS AND METHODS FOR REHABILITATING ALCOHOL

TECHNICAL FIELD

The invention disclosed herein relates generally to the field of alcoholic beverages, and more particularly, to systems and methods for removing adverse congeners from alcoholic solutions.

BACKGROUND

Alcoholic beverages have been a staple of humanity for thousands of years. Beer was instrumental in the building of the Egyptian pyramids as both inexpensive and enjoyable rations for the labor force, but also a means of converting non-potable water into a source of hydration. However, despite millennia of experience in fermenting and distilling alcoholic beverages, it remains difficult to consistently produce high-quality beer, wine and liquor. Indeed, the quality of wine and liquor especially run the gamut from the very rare and fine to the barely drinkable.

The art of rafting of alcoholic beverages has remained a closely guarded trade for many years. Typically, aqueous solutions sweetened with a start of fruit sugar are fermented to produce ethyl alcohol as well as a variety of congeners (minor chemical constituents). While some of these congeners are desired as providing a certain richness of flavor, several others, such as methanol, acetaldehyde, butanol, isobutanol, methylbutanol, and the like, are known to cause hangover symptoms and/or impart a harsh flavor to the alcoholic beverage. While barrel aging alcohol is known to absorb some of the larger congener molecules and thus improve the taste of the alcohol, such a process is extraordinarily time consuming, often taking decades.

Beverage quality may vary greatly from manufacturer to manufacture, as well as from batch to batch produced by a given manufacturer. This arises in part because of inconsistent processing and in part due to variations in the source and quality of raw materials. One source of variance in beverage quality is the presence of unwanted chemical species or congeners in the beverage generated as side effects of the fermentation/distilling processes and contributing adverse flavors to the beverage.

Many of these chemical species have boiling points very close to ethanol at standard pressure, and are hard to remove by distillation without simultaneously removing substantive quantities of ethanol. Thus, there remains a need for means to quickly remove unwanted congeners from alcoholic beverages while leaving behind the ethanol and desired congeners/flavorings. The present novel technology addresses this need.

BRIEF DESCRIPTION OF THE DRAWINGS

FIG. 1A is a perspective view of an alcohol rehabilitation system according to a first embodiment of the present invention.

FIG. 1B is a side elevation view of the system of FIG. 1A.

FIG. 1C is a cutaway view of the system of FIG. 1B along line A-A'.

FIG. 4C is a front view of the alcohol rehabilitation system of FIG. 4A.

DETAILED DESCRIPTION

Figure 1D:
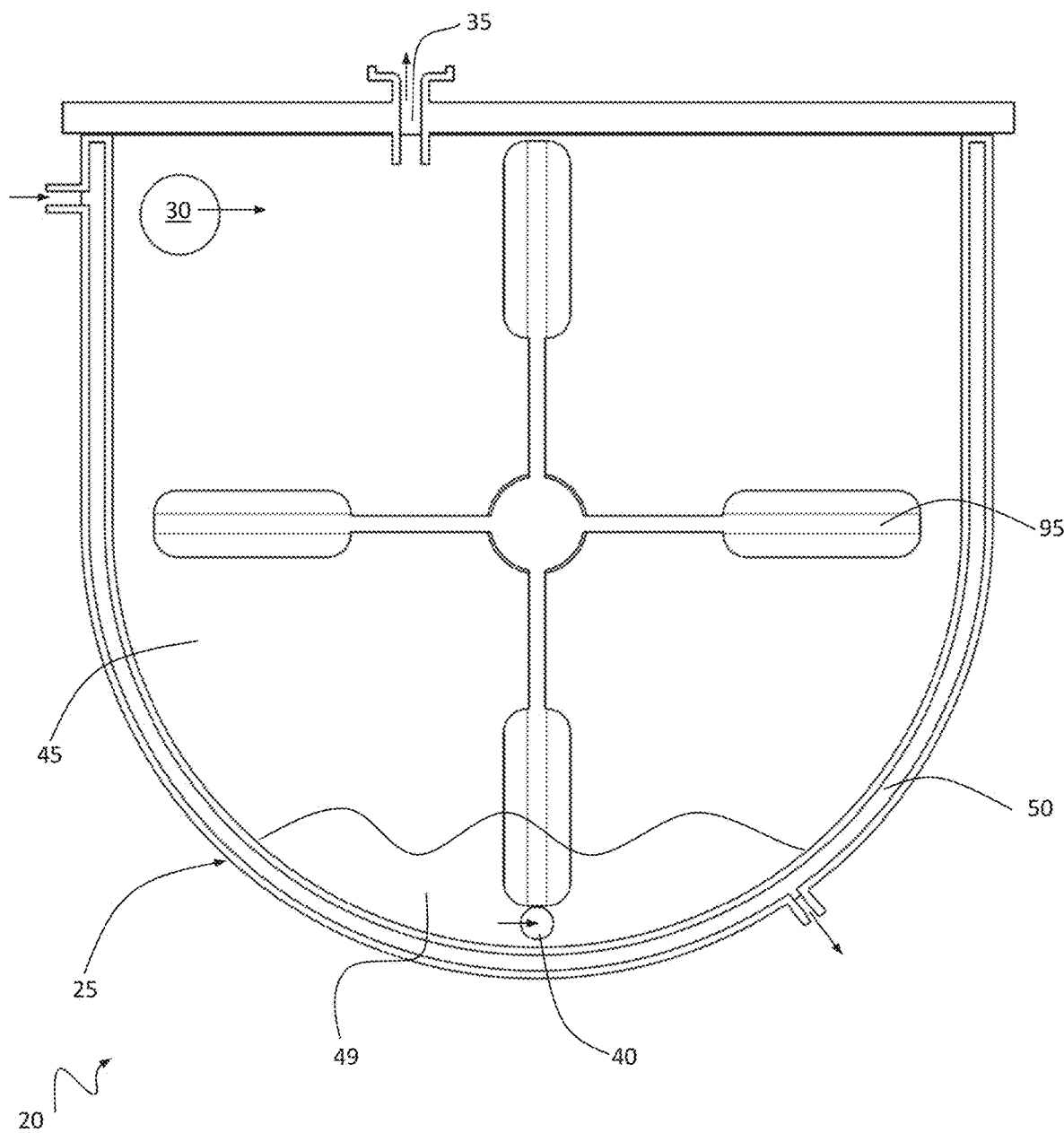
FIG. 1D is a cutaway view of the system of FIG. 1A showing internally mounted agitators.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As shown in FIGS. 1A-8, the present novel technology relates to an apparatus 20 for preferentially removing predetermined unwanted congeners from alcoholic solutions such as beer, wine, liquor, and like beverages. The apparatus 20 includes a pressure vessel 25 having a liquid inlet port 30, a vapor outlet port 35, and a liquid outlet port 40, all in fluidic communication with an internal pressure controllable chamber 45 defined by the pressure vessel 20. The pressure vessel 25 typically includes a water jacket 50 or like temperature controller at least partially enveloping the pressure chamber 45 and in thermal communication with the same. Liquid inlet port 30 is typically connected in fluidic communication, such as via a pipe 55, with a liquid pump 60. Pump 60 is connected in fluidic communication with alcohol source 65. Typically, at least one valve 70 is operationally connected in line between alcohol source 65 and liquid inlet port 30. The valve 70 may be connected between inlet port 30 and pump 60, between pump 60 and alcohol source 65, or valves 70 maybe connected in both positions. As used herein, alcohol may mean beer, wine, liquor, or any ethanol solution.

Vapor outlet port 35 is typically connected in fluidic communication with a vacuum pump 75, which is connected in fluidic communication with a collection vessel 80. Vacuum pump 75 typically operates to remove and direct evolved vapor from the pressure vessel 25 for collection in the collection vessel 80 at a desired pressure, as well as establish a partial vacuum within the pressure controllable chamber 45. The collection vessel 80 may be a cold trap, a pressure-controlled vessel, or the like. Typically, at least one valve 70 is operationally connected in line between collection vessel 80 and vapor outlet port 35. The valve 70 may be connected between vessel 45 and pump 75, between pump 75 and outlet port 35, or valves 70 maybe connected in both positions.

Liquid outlet port 40 is typically connected in fluidic communication with pump 85, which is connected in fluidic communication with alcohol collection vessel 90. Typically, at least one valve 70 is operationally connected in line between alcohol collection vessel 90 and liquid outlet port 40. The valve 70 maybe connected between vessel 45 and pump 85, between pump 85 and collection vessel 90, or valves 70 may be connected in both positions.

Example 1

As illustrated generally in FIGS. 1A-1E, the above described assembly 20 may be embodied to treat ethanol solutions on a batch-by-batch basis. Pressure vessel 25 includes ports 30, 35, 40 as described above, as well as water jacket 50 or like temperature control mechanism encapsulating pressure chamber 45 in thermal communication therewith. Agitator 95 is positioned within pressure chamber 45 to facilitate stirring/vibration/bubbling of a volume of alcoholic beverage contained therein. A partial vacuum in pressure chamber 45 may be established via energization of vacuum pump 75.

Figure 1E:
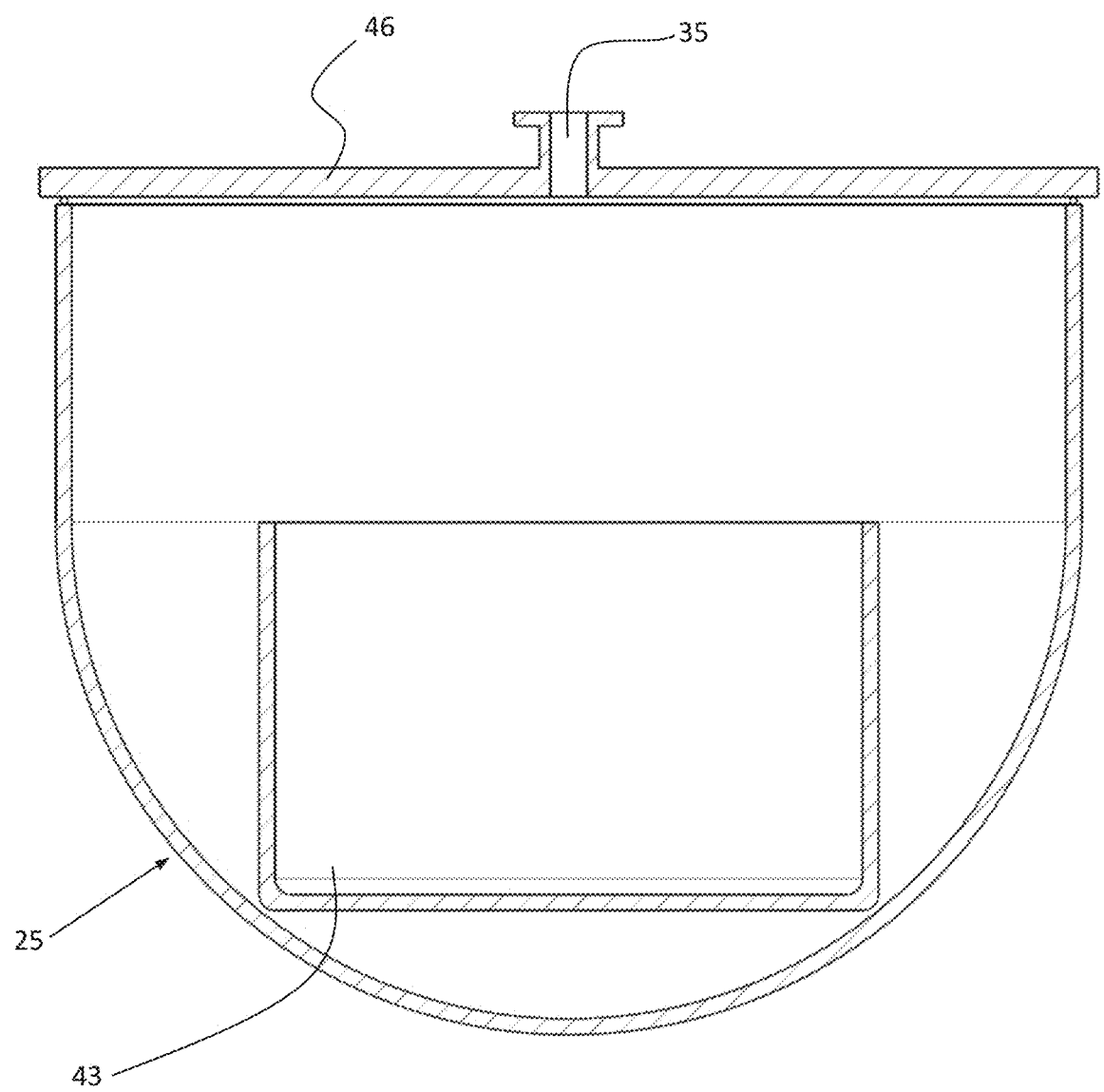
FIG. 1E is a cutaway section view of the alcohol rehabilitation system of FIG. 1A with a secondary open container positioned therein.

In FIG. 1E, an ethanol solution contained in an open container 43 is placed in the pressure chamber 45. A vacuum lid 46 is then engaged with the vacuum chamber 45, thereby isolating the vacuum chamber environment from the surrounding exterior environment, and the pressure in the vacuum chamber 45 is decreased by energization of a vacuum pump 75 in operational communication with the vapor outlet port 35. Once the vacuum chamber pressure reaches a specified level, the vacuum chamber pressure is then increased to atmospheric pressure and the lid 46 is removed, followed by the container 46 containing the now vacuum-treated ethanol solution.

Example 2

Figure 2:
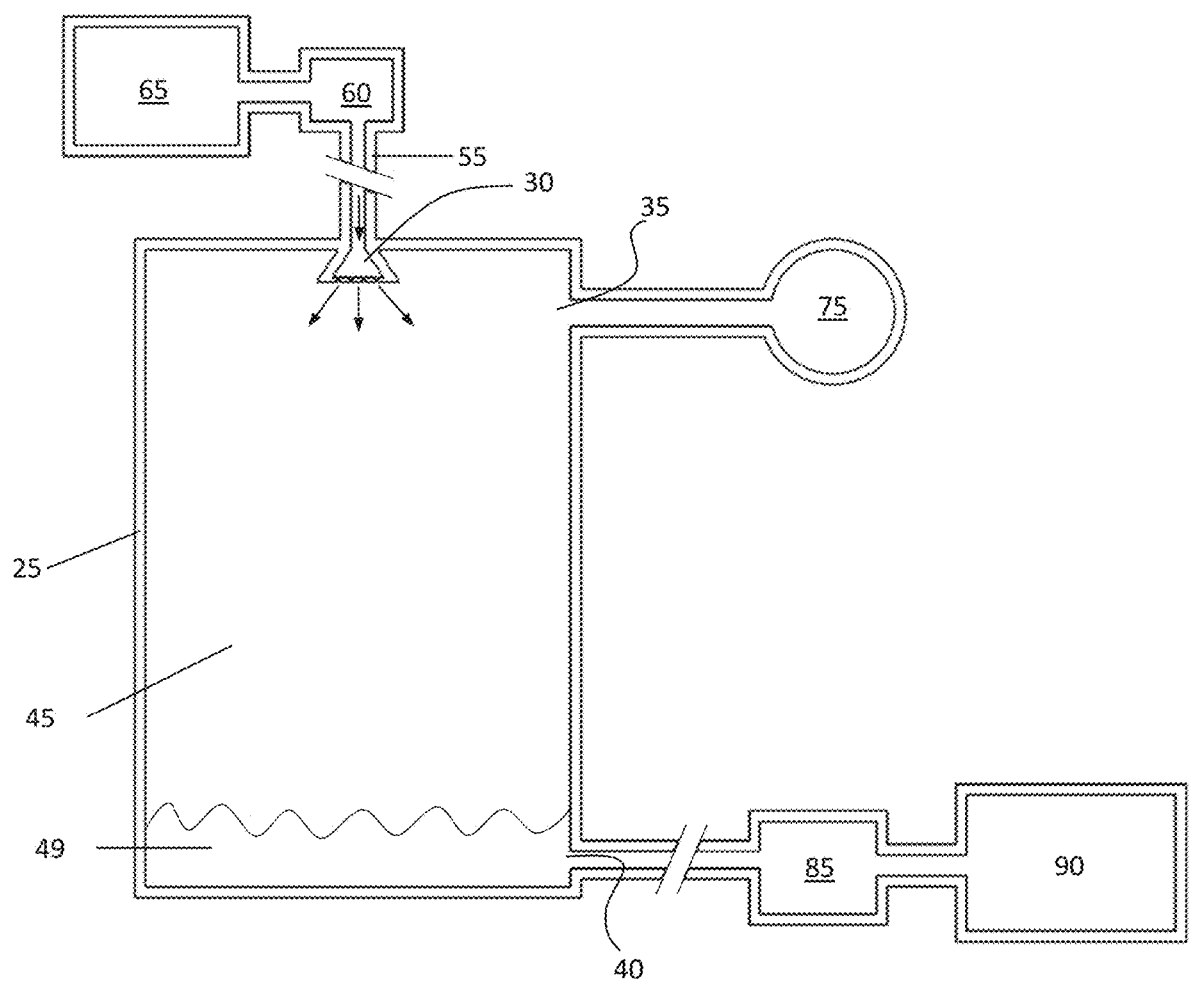
FIG. 2 is a cutaway section view of an alcohol rehabilitation system according to a second embodiment of the present invention.

As illustrated in FIG. 2, the above described assembly 20 may take an embodiment to treat ethanol solutions as a continuous flow process. Liquid inlet port 30 is configured as a spray head and is positioned to spray ethanol solution pumped from source tank 65 into the pressure chamber 45 already pumped down to the desired partial vacuum pressure. The spray of ethanol solution travels through the pressure chamber 45 to collect or pool at the bottom of the pressure vessel 25, where it maybe pumped out through outlet port 40. In some embodiments, inlet port 30 is configured as a nozzle, while in other embodiments a separate nozzle is operationally connected to inlet port 30 to accelerate and direct the incoming liquid.

Example 3

Figure 3:
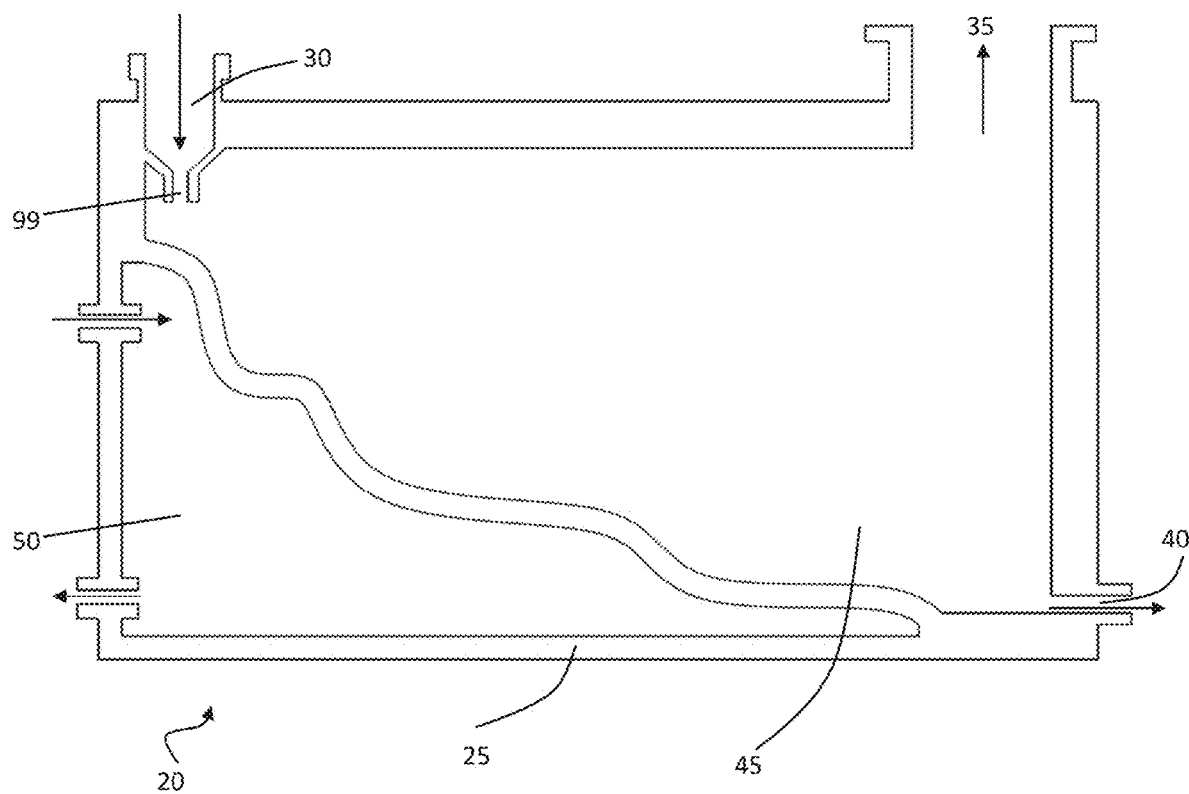
FIG. 3 is a cutaway section view of an alcohol rehabilitation system according to a third embodiment of the present invention.
Figure 4A:
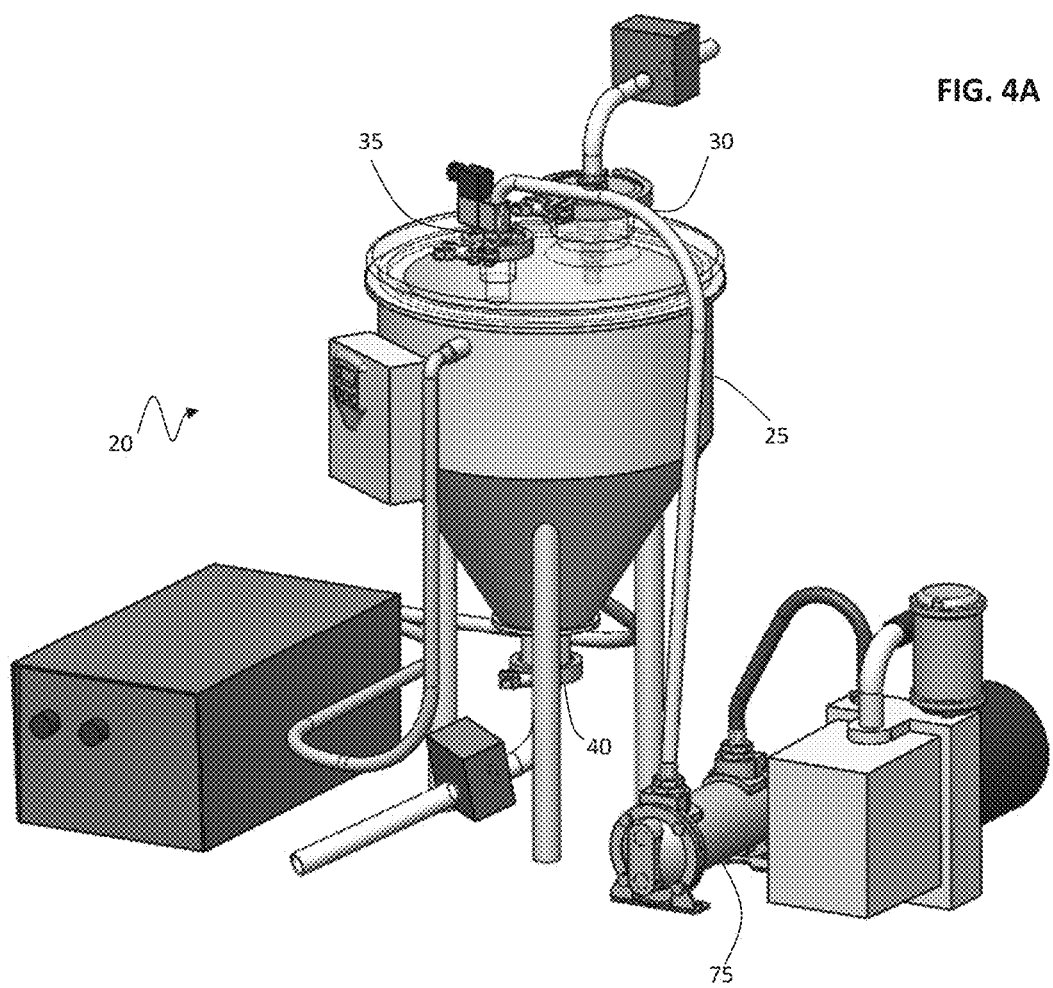
FIG. 4A is first perspective view of an alcohol rehabilitation system according to fourth embodiment of the present invention.
Figure 4B:
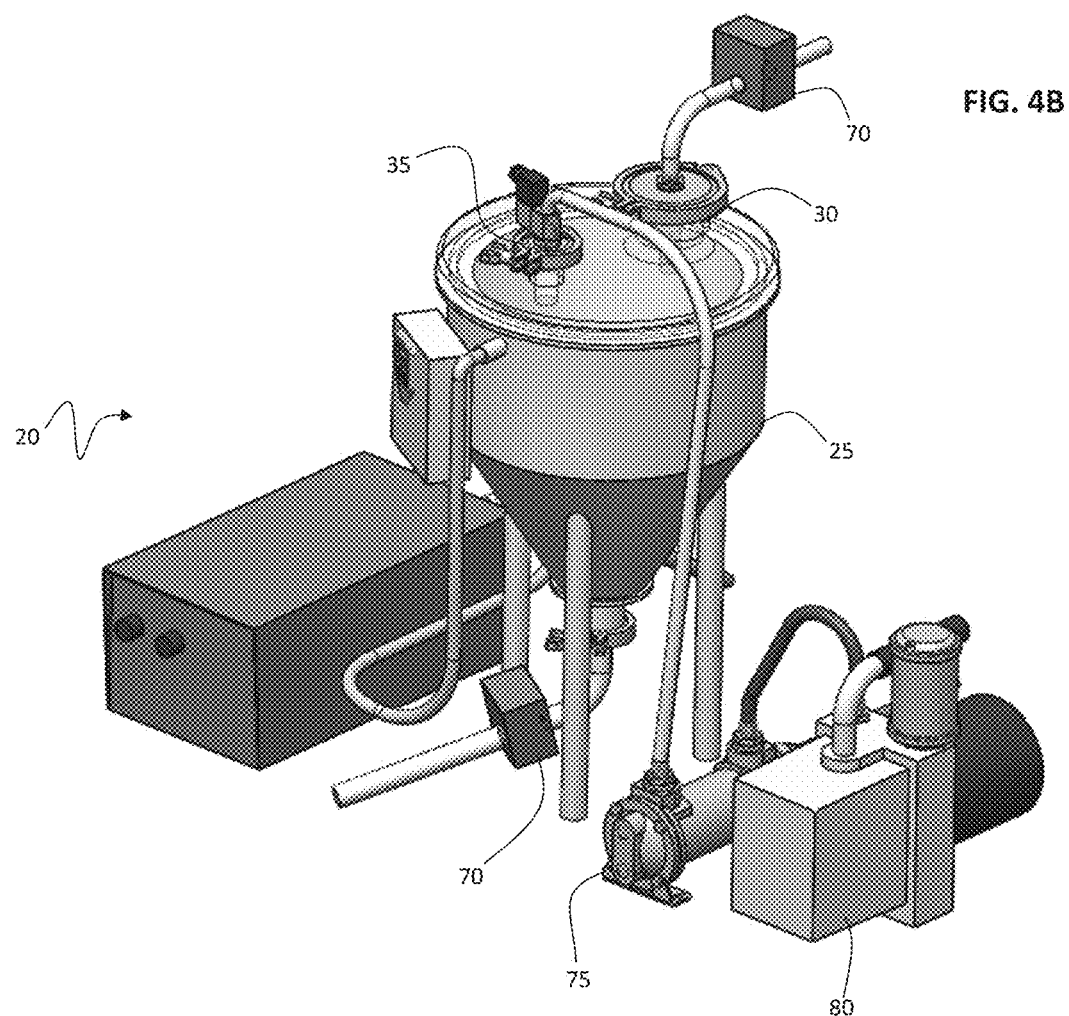
FIG. 4B is a second perspective view of the alcohol rehabilitation system of FIG. 4A.
Figure 4D:
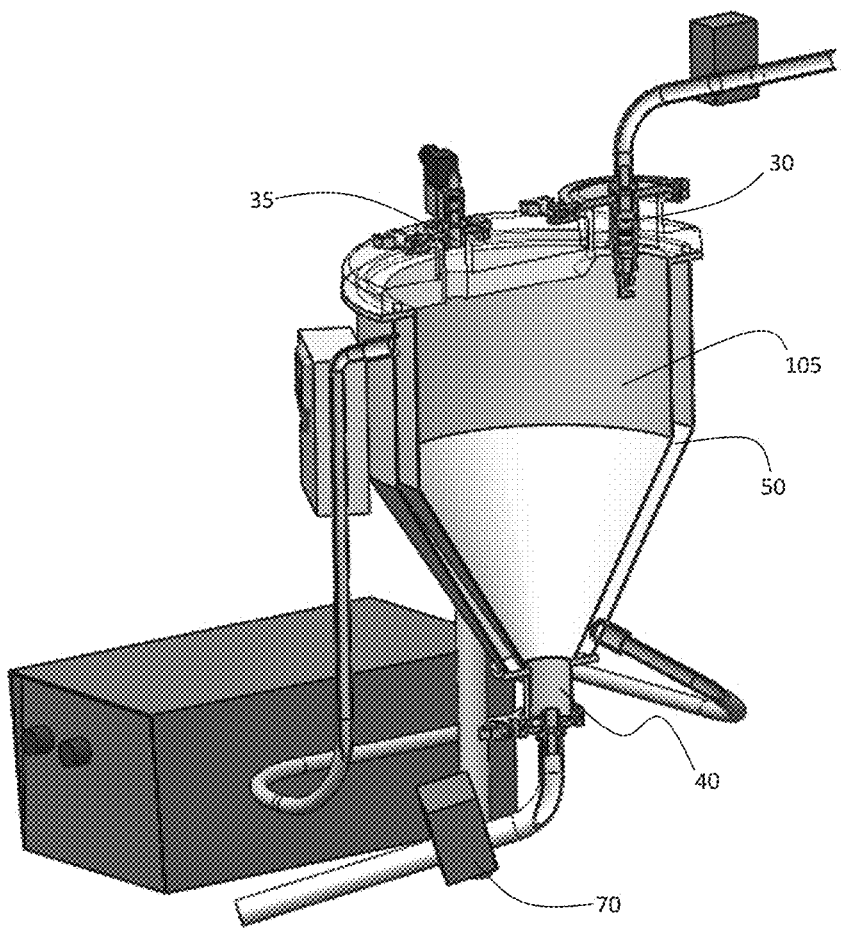
FIG. 4D is a first cutaway view of the alcohol rehabilitation system of FIG. 4A having a smooth interior wall.
Figure 4E:
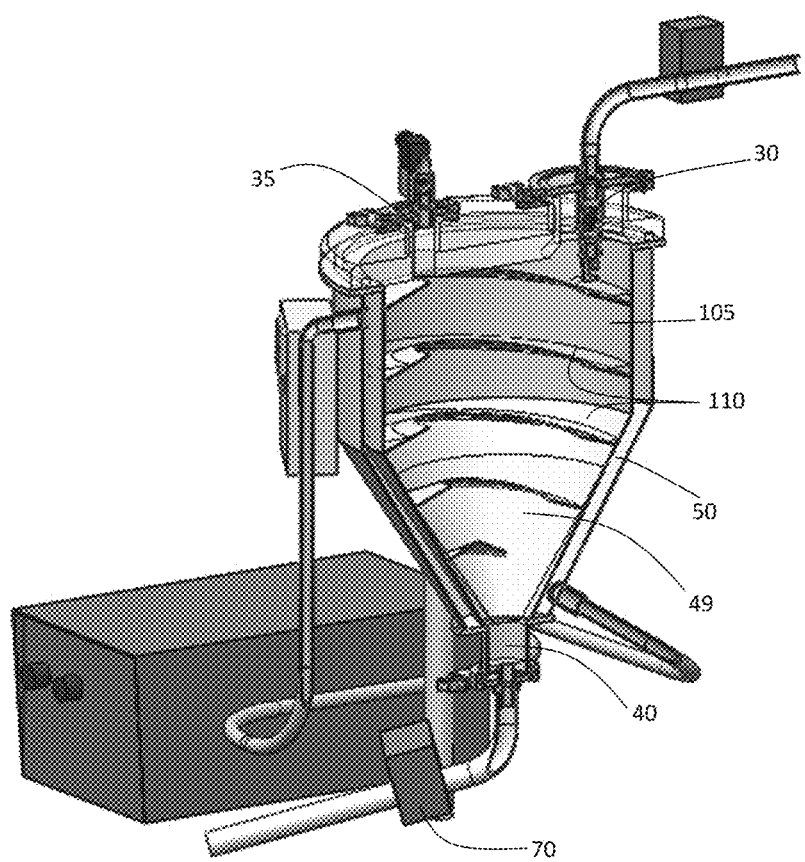
FIG. 4E is a second cutaway view of the alcohol rehabilitation system of FIG. 4A having a raced interior wall.
Figure 4F:
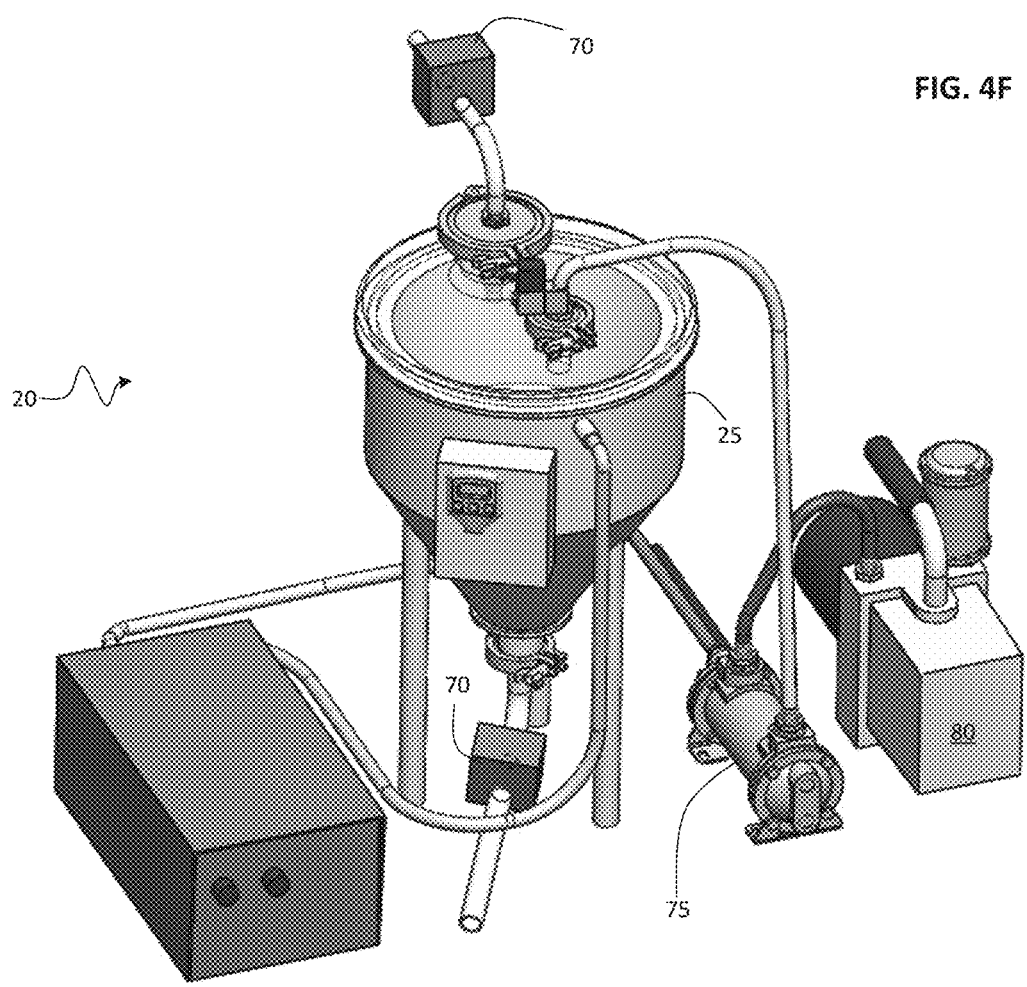
FIG. 4F is a third perspective view of the alcohol rehabilitation system of FIG. 4A.

As illustrated in FIG. 3, the above described assembly 20 may take another embodiment to treat ethanol solutions as a continuous flow process. The liquid inlet port 30 may empty onto one end of a ramp 100 where ethanol solution pumped from source tank 65 spreads into a thin layer or sheet and flows downhill to pool at the other end of the ramp 100. Congeners may be evolved from the flowing ethanol sheet into the partial vacuum environment inside the pressure chamber 45 when the vacuum pump 75 is energized. The treated ethanol solution may be pumped out of pressure chamber 45 and into collection vessel 90.

Example 4

As illustrated in FIGS. 4A-4E, the above described assembly 20 may take still another embodiment to treat ethanol solutions as a continuous flow process. Vessel 25 is typically acorn-shaped, with a circular top to bottom cross-section that decreases in diameter from top to bottom (in this example, the top down sectional profile has a cylindrical portion atop a conical portion), and a chevron-shaped side sectional profile (in this example, the side sectional profile has a rectangular upper portion and a triangular lower portion). Vessel typically includes a water jacket exterior 50 encasing a pressure controllable chamber interior 45. Liquid inlet port 30 positioned near the top of the vessel 25 injects ethanol solution pumped from tank 65 into pressure chamber 45 wherein injected ethanol solution is under sufficient pressure upon injection to be moving quickly enough to follow a spiral path along the inside of the pressure chamber 45 and ultimately pool at the bottom. Typically, the ethanol solution defines a thin stream or ribbon that circles the vessel 25 a plurality of times while the partial vacuum therein (as provided by the energized vacuum pump 75 connected in fluidic communication therewith) evolves unwanted congeners therefrom to yield a treated and purified ethanol solution. The purified ethanol solution pools at the bottom of the pressure chamber 45 and may be pumped therefrom via liquid pump 85 into collection vessel 90. In some embodiments, the inside wall 105 of pressure chamber 45 is grooved or contoured no to help guide flowing ethanol solution in a helical path from inlet port 30 to outlet port 40. Typically, the inside wall 105 would include a helical groove or race 110 to guide inlet liquid from the inlet port 30 around the inner wall several times to the outlet port 40.

In other like embodiments, vessel 25 may have convex or concave (see FIG. 5A) interior sectional contours. A concave shape profile may enable slow post inlet port liquid flow, followed by a deep cavity or reservoir formed near the outlet port 40 for sump modulation.

Ports 30, 35, and 40 of a first pressure chamber 45 maybe in connected fluidic communication with other ports 30, 35, and 40 of other similar or identical pressure chambers 45 such that a plurality of pressure chambers 45 maybe run in parallel from central vacuum 75 and fluidic pumps 60, 85. In this embodiment, fluid maybe regulated individually or at fluidic manifolds connected in liquid communication with each respective pressure chamber 45.

In some embodiments, a floater valve 91 maybe used to prevent dry sump of the liquid outlet port 30 and regulate a minimum sump level. Under operation a floating valve 91 may open the liquid outlet port 40 once sufficient liquid enters the chamber 45. In the case where the liquid outlet pump 85 removes liquid sufficiently fast to decrease the liquid below float level, the floater valve 91 may form a pressure gradient between the vessel 45 and liquid outlet pump 85 preventing further liquid removal. One added benefit of a floater valve 91 is to prevent vessel atmosphere from being pressurized back into the cleaned or treated liquid leaving the liquid outlet port 40.

Sensors 93 may also be used to provide feedback to regulator valves 94 to maintain a positive volume above liquid outlet port 40 and prevent depressurization of vessel atmosphere in the process fluid. Sensors 93 may be in direct communication with the vessel sump liquid (typically vacuum-treated ethanol solution), such as in the case of optical, inductive, or acoustic sensors 93, or indirectly monitor the fluid level with an acoustic, ultrasonic, or thermal sensors 93 around the fluid outlet port 40.

Liquid pumps 60, 85 as described herein maybe variable displacement pumps, in the case of diaphragm pumps or piston pumps, or maybe fixed displacement pumps, in the case of turbine pumps. Fluidic pumps 75, 85 in communication with the outlet ports 35, 40 may experience thirteen to fifteen PSI of negative pressure and may need to be combined in series to provide sufficient suction; as used herein, 'vacuum pump' may mean a single pump unit or a plurality of pump unites operationally connected in series. An intermediate re-pressurization chamber 98 may also be used between multiple fluidic pumps 60, 85.

Vacuum pumps 75 of the present disclosure maybe variable displacement pumps, such as piston pumps, rotary screw pumps, or rotary vane pump, or fixed displacement pumps, in the case of multi-stage regenerative blowers. Cold traps of the present novel technology may also result in pressure gradients and function as vacuum pumps. Cold traps may be electrically cycled, or may be fed using cryogenic media, such as dry ice or liquid nitrogen.

Fluid flow maybe regulated by modulating valve cross-sectional area, or by repeatedly opening and closing the valve. Automated valves may be energized, such as pneumatically or electrically.

A fluid inlet nozzle maybe connected in fluidic communication with inlet port 30 to direct the flow of the liquid into the vessel 45. The liquid may flow directly along the gravitational path or may flow in a helical manner as it proceeds down an interior vessel wall. Helical paths maybe used to increase retention time and disrupt the surface tension of the fluid, and may benefit from a nozzle 99 with a narrowing throat to increase velocity prior to injection resulting in increased retention times for longer exposure to vacuum conditions. The terminal end of a fluid inlet nozzle 30 may be located sufficiently close to a vessel wall 105 to prevent droplet formation and splashing, with typical distances less than fifteen centimeters and typically less than two centimeters from the vessel wall 105. Laminar flow inlets may be used to decrease splashing and volatilization occurring during injection. Alternatively, a single or a plurality of liquid inlet openings 30 may enable a quasi-uniform flow of liquid to sheet along the inner wall of the vessel 45 to the liquid outlet port 40.

Figure 5A:
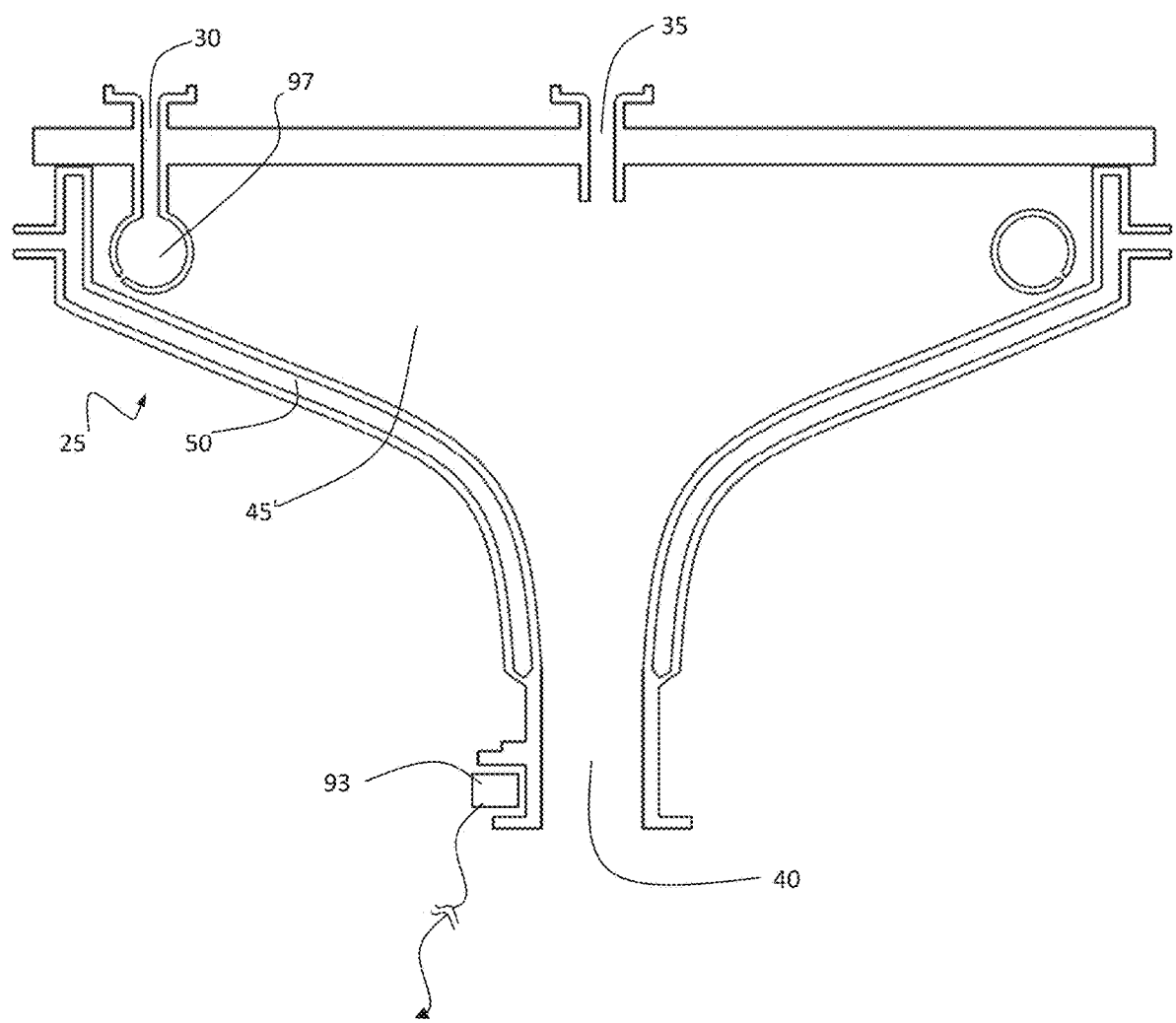
FIG. 5A is a cutaway view of pressure vessel of the embodiment of FIG. 4A wherein the vessel has concave interior sidewalls and features a fluid inlet body (manifold).
Figure 5B:
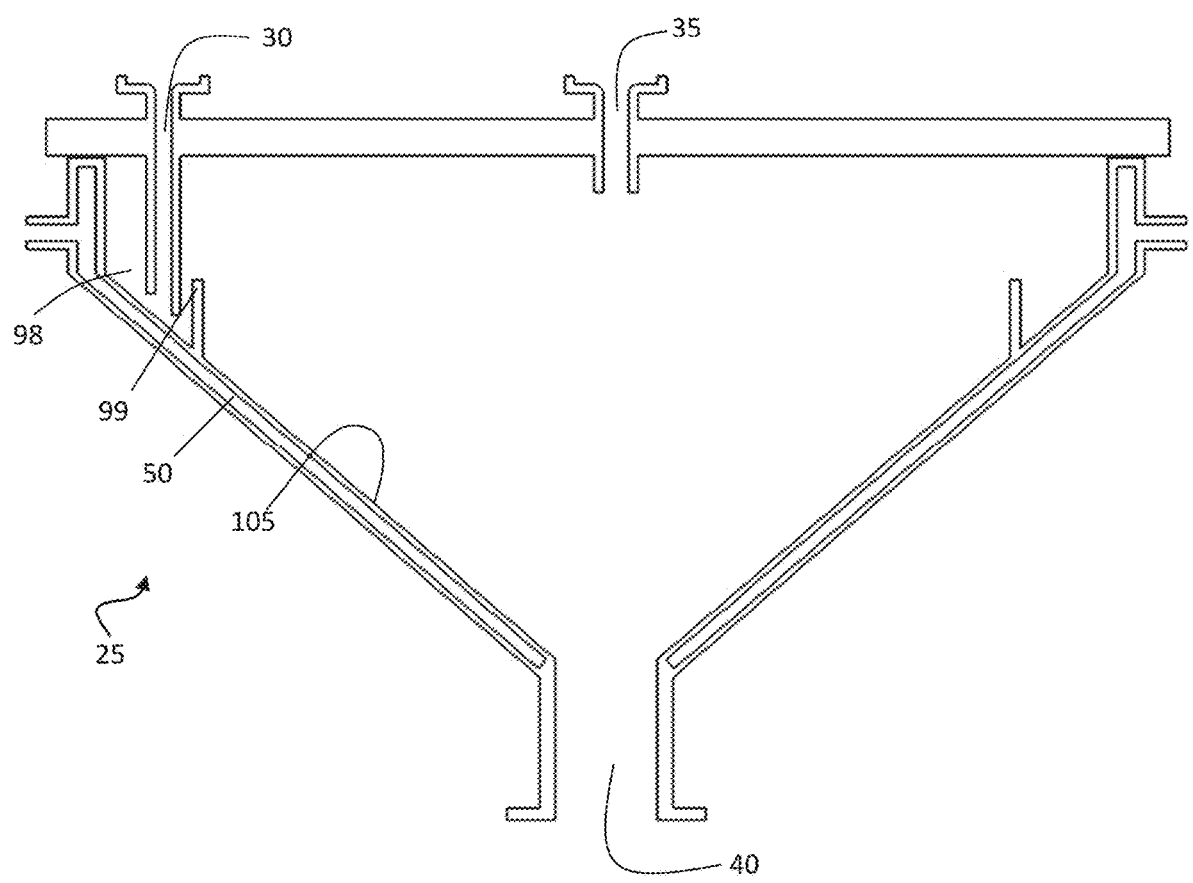
FIG. 5B is a cutaway view of pressure vessel of the embodiment of FIG. 4A wherein the vessel has an inlet trough operationally connected to the inlet port.
Figures 6A, 6B:
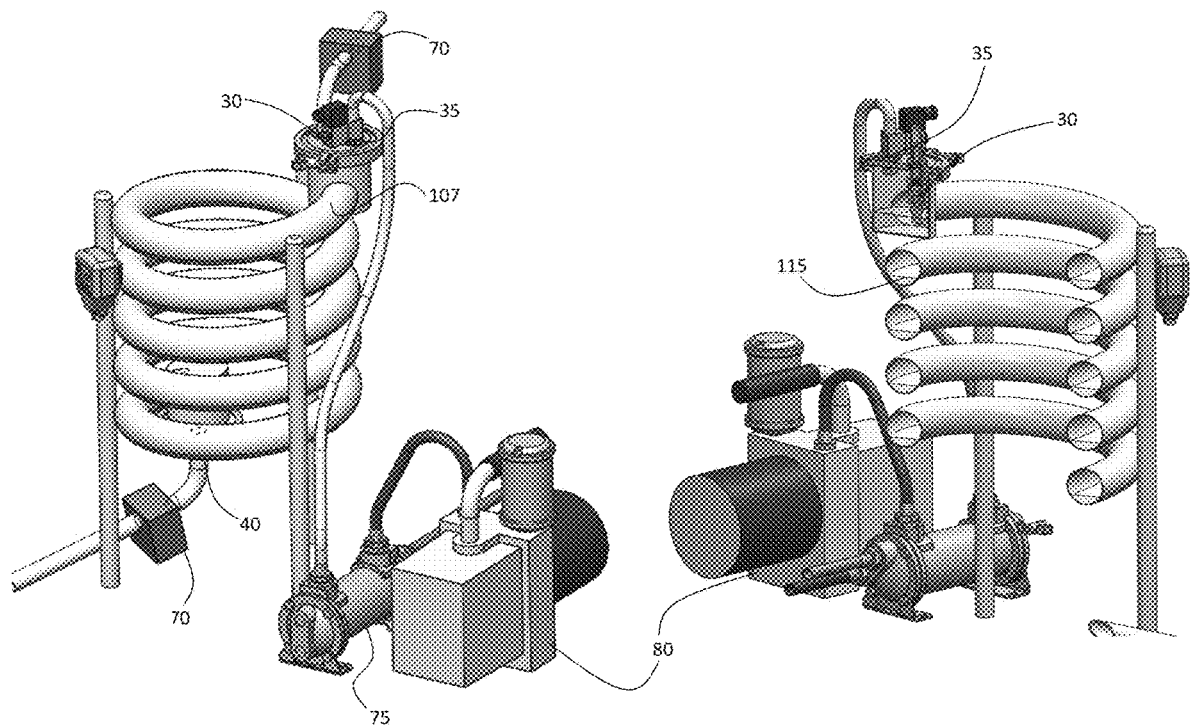
FIG. 6A is perspective view perspective view of an alcohol rehabilitation system according to fifth embodiment of the present invention.
FIG. 6B is a cutaway view of the embodiment of FIG. 6A.
Figure 7:
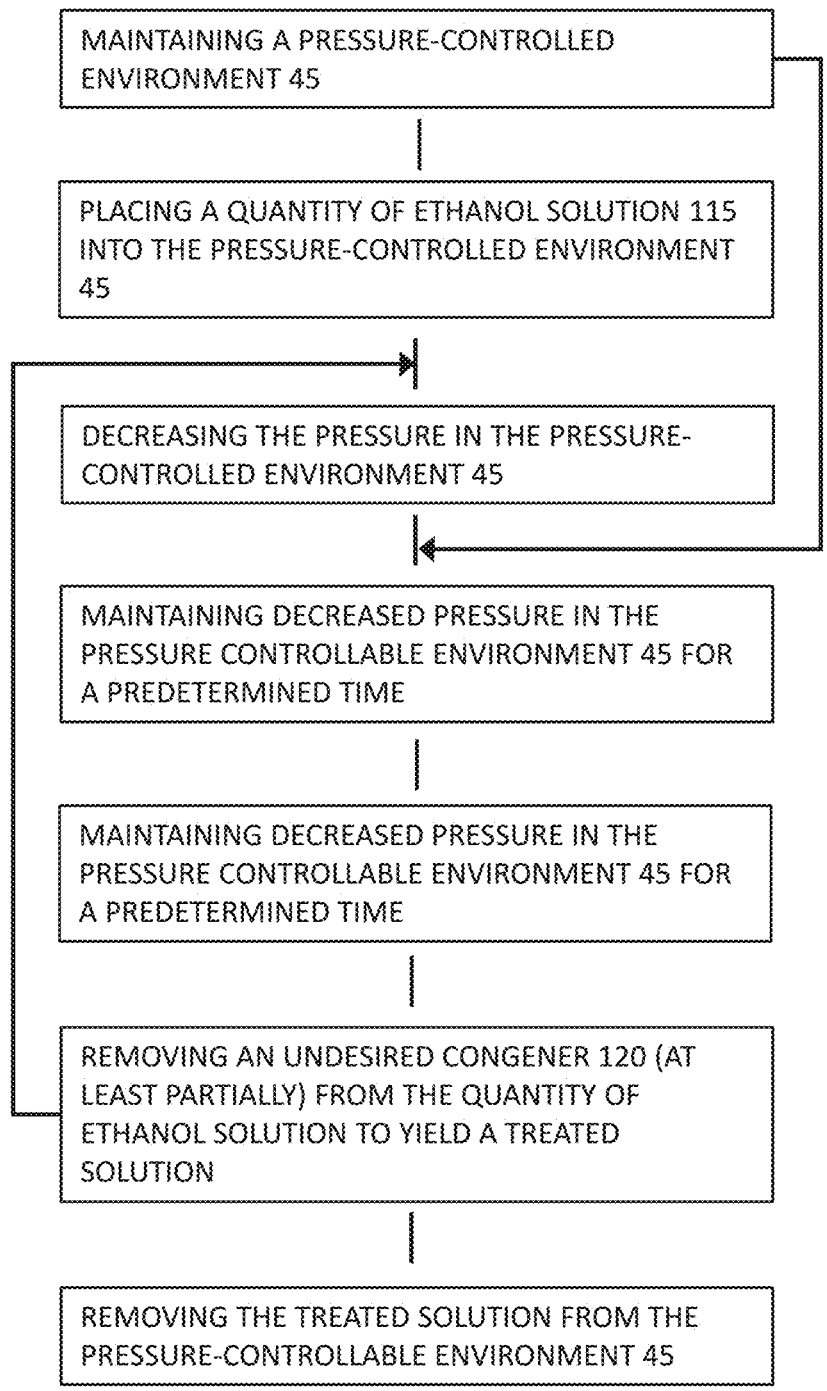
FIG. 7 is a schematic view of a method for rehabilitating alcohol underlying the operation of the above embodiments.
Figure 8:
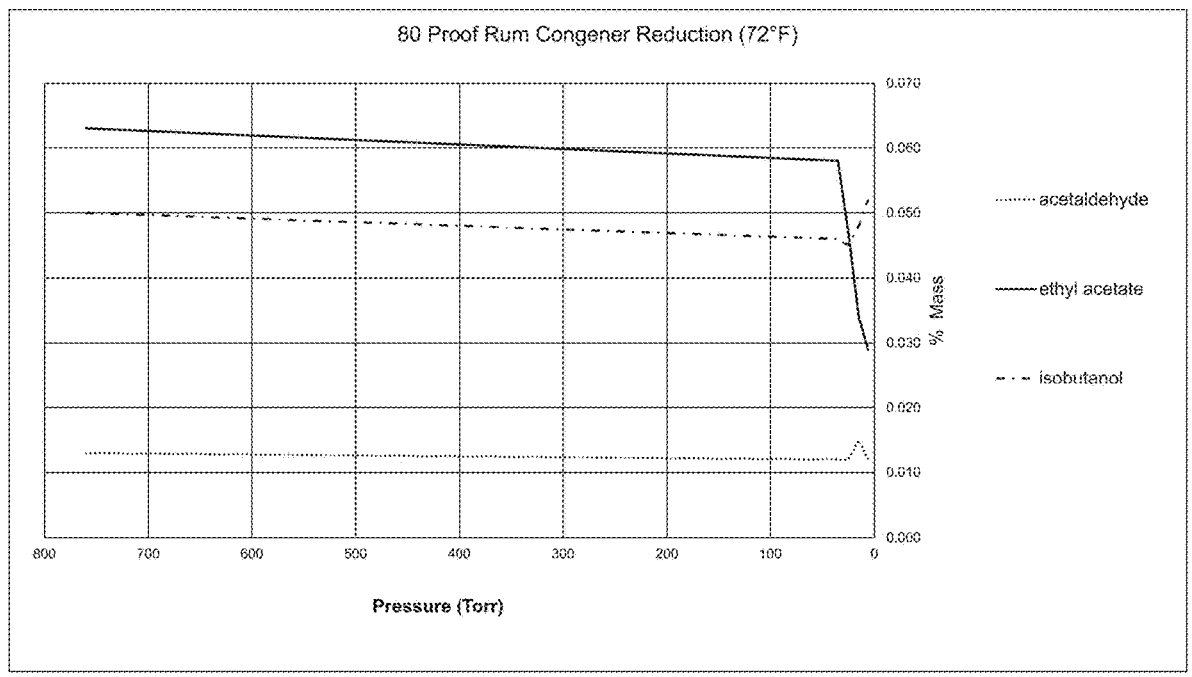
FIG. 8 is a graph of mass percent of congeners as a function of treatment pressure for an ethanol solution (rum).

A liquid inlet body 97 maybe used to decrease the pressure drop between a pressure regulator and vacuum vessel 45 by enabling liquid accumulation prior to injection (see FIG. 5A). In this case, liquid enters a manifold 97 a volume of space, such as a large tube, at least partially encircling the upper lip of the vessel 45. The cross-sectional area of the inlet body 97 is large relative to the inlet valve 31 enabling fluid to partially decrease in pressure prior to entering the vessel 45, which enables lower head pressures and slower flow. In another embodiment the liquid inlet body 97 may comprise bilateral pieces that may or may not be incorporated into the lid of the vessel. Bilateral separation may be used to enable rapid disassembly.

In one embodiment, the inlet body is maintained above 35 torr, while the vessel is maintained below 35 torr. In this case pressure may be substantially decreased without significantly altering the liquid composition prior to entering the bulk vessel volume.

A separate pressure drop vessel maybe used to gradually step the pressure of the liquid down prior to entering the vessel 45. Preferably the pressure drop vessel would be maintained above 35 torr.

In another embodiment (FIG. 5B), liquid enters vessel and is collected in trough 98. Once trough 98 has filled, liquid will pour over the trough and sheet down the sidewalls 105 toward sump 49. The trough 98 may fill to a level defined by a lip 99 until it flows over the lip 99 forming a sheet of liquid across the vessel wall 105.

Vessel 25 maybe constructed of metal, such as stainless steel, copper or aluminum, or plastic, such as polycarbonate or PETG, or a combination thereof. The liquid may directly contact the inner wall 105 of the vessel 45, or may contact a surface liner disposed within and either isolated from, or disposed against the vessel wall 105.

A water jacket 50 maybe constructed of a bulk volume between the inner vessel wall and a partially encapsulating wall defining a single thermal zone, or may comprise multiple thermal zones. Multi-zone cooling maybe fabricated through the use of bulkheads or pillow plate in the case of stainless steel.

The inner wall 105 of the vacuum chamber 45 maybe smooth or even polished, or may be deliberately etched and roughened to promote the evolution of bubbles. A smooth vessel wall 105 will promote liquid flow during helical circulation, while a rough or etched surface may retard liquid flow and result in increased liquid retention times in the case of liquid following a gravitational trajectory along the vessel wall 105.

In another embodiment of the present invention, liquid flow is introduced uninterrupted from the inlet port 30 to the liquid sump 49 without contacting the vessel wall 105. In this case the liquid passes or falls straight through the vessel 45 unimpeded and is outgassed during decent.

In still another embodiment (see FIGS. 6A and 6B), pressure vessel 25 has the form of spiral tube, with liquid inlet and gas outlet ports at a first, typically elevated, end 107 and the liquid outlet 40 positioned at the opposite end 109. Liquid typically travels from one end 107 to the other 109 as urged by gravity.

In operation, a predetermined quantity of an ethanol solution 115, such as beer (typically prior to bottling), wine, liquor, or the like is inlet into pressure chamber 45. Typically, the ethanol solution 115 enjoys a high surface area-to-volume ratio during residence in the pressure chamber 45, such as in the form of droplets or a thin sheet or ribbon, so that predetermined undesired congeners 120 may be more quickly and efficiently evolved therefrom. The atmosphere in the pressure chamber 45 is below atmospheric pressure (i.e., a partial vacuum) to encourage the preferential evolution of one or more unwanted congeners 120 from the solution 115. The present invention takes advantage of complex intermolecular forces in fermented liquids at low temperatures and pressures. Conventionally one would expect acetaldehyde to be removed under vacuum before ethyl acetate due to its acetaldehyde's higher vapor pressure and lower boiling point. In fact, acetaldehyde and isobutanol remain relatively unchanged in the present system while the ethyl acetate is selected removed, which cannot be understood by simply comparing boiling points and vapor pressures. Furthermore, ethyl acetate in high concentrations is offensive; however, at lower concentrations it maybe desirable. The present method enables the selective control over the amount of ethyl acetate removed based on the temperature and vacuum pressure for a given retention time. This selectivity occurs over a vary narrow pressure range. As a result, artisans may reliably tune the level of ethyl acetate in alcoholic beverages to create a desired flavor profile. This evolution of undesirable congeners 120 takes advantage of the fact that while such congeners 120 have boiling points quite close to ethanol at atmospheric pressure, the same congeners 120 have boiling points substantially different from, and typically lower than, ethanol at reduced pressures and the presence of multiple congeners in solution effects the relative boiling points of the other congeners. Thus, exposure of the ethanol solution to reduced pressures (partial vacuums) allows for the preferential evolution of certain congeners 120, such as ethyl acetate, leaving behind the ethanol with certain desired lower boiling point congeners still in solution therewith (see FIG. 8).

In the case of a batch treatment, the liquid ethanol solution 115 is loaded into the pressure chamber 45, the pressure chamber 45 is sealed pressure tight, and the pressure therein is reduced to the desired partial vacuum pressure. In the case of continuous flow treatment, the pressure within the pressure chamber 45 is maintained at the desired partial vacuum pressure and the ethanol solution 115 is flowed therethrough at a predetermined desired rate.

By holding the atmosphere in the pressure chamber at ambient temperature and at a reduced pressure (such as forty-five to five Torr, more typically thirty to fifteen Torr, still more typically twenty-eight to eighteen Torr, and yet more typically twenty-five Torr), ethyl acetate may be substantially removed from an ethanol solution 115 without substantially decreasing the ethanol content of said solution 115. Residence time for flowing ethanol solution 115 is typically no more than about sixty seconds, more typically no more than about twenty seconds, and more typically no more than about five seconds. In the case of the batch style assembly apparatus, residence time for the ethanol solution 115 under vacuum may be longer. Moreover, as the vacuum partial pressure decreases, residence time of the ethanol solution 115 may likewise decrease. In general, for a given congener, the liquid temperature may vary from about negative twenty degrees Celsius to about eighty degrees Celsius, more typically from about zero degrees Celsius to about sixty degrees Celsius, still more typically from about ten degrees Celsius to about thirty-five degrees Celsius.

In each of these embodiments, the ethanol solution 115 remains liquid throughout the vacuum treatment process and throughout exposure to the reduced pressure environment in the pressure chamber 45. While the evolved congeners 120 change phase from liquid to gas the ethanol solution remains liquid, meaning that there is no distillation and/or recondensation or reconstitution of the ethanol solution 115 during processing in the pressure chamber.

One typically undesirable congener is ethyl acetate. Ethyl acetate and ethanol have very similar boiling points at atmospheric pressure, but dissimilar boiling points at pressures from five and thirty-five Torr, with ethyl acetate having a significantly lower boiling point. By maintaining a pressure of between five and thirty-five Torr in the pressure chamber 45 and controlling the temperature within the pressure chamber 45 to be about twenty-two degrees Celsius, ethyl acetate maybe preferentially or substantially completely removed from ethanol solution leaving substantially all of the ethanol therein. Typically, at least one third of the ethyl acetate is removed, more typically at least one half is removed, still more typically at least two-thirds is removed, and yet more typically substantially all the ethyl acetate is removed from the ethanol solution. As used herein, preferentially removing an unwanted congener, such as ethyl acetate, means removing some or all of the unwanted congener from solution without substantially removing any of the other constituents of the solution. Typically at about twenty-five Torr and twenty-two degrees Celsius, between forty and sixty percent of the ethyl acetate content is removed in about five seconds.

Looked at another way, the typical ethanol solution beverage has between about 0.05 percent and 0.25 percent ethyl acetate content. The instant alcohol rehabilitation treatment typically reduces that amount to about fifty percent or less of the original ethyl acetate content. The target amount is determined by a number of factors, including personal taste and type of alcoholic beverage. For example, a rum sample having an initial content of about 0.064 percent may be treated to leave only below 0.05 percent, more typically to below 0.04 percent, still more typically to below 0.03 percent, and yet more typically to below 0.02 percent. A bourbon initially having 0.14 percent ethyl acetate may be treated to leave about 0.051 percent ethyl acetate as an optimal amount. A good rule of thumb is to reduce the ethyl acetate content to about half the original content, or to between forty and sixty percent. All values are given as weight percent, and water content is ignored such that all values relate to the ethanol distillate fraction of the overall ethanol solution.

By selecting other treatment temperature/pressure/residence time combinations, other congeners my likewise be selectively removed. In some embodiments, temperature sensors and/or pressure sensors and/or chemical sensors (or combinations of the same) are positioned in thermal communication with the interior of the vessel 25 and/or the water jacket and/or the vapor outlet port (or combinations of the same). These sensors may be operationally connected to an electronic controller that may likewise be connected to one or more of the pumps 60, 75, 85 and/or ports 30, 35, 40 and/or valves 70 and/or agitators 95 (if present) to provide feedback-based control of the process to maintain the process within predetermined parameters and/or within predetermined pressure/temperature profiles. In some embodiments, the temperature and pressure within the chamber maybe varied during residence of the ethanol solution 115 to selectively target and remove a plurality of undesired congeners 120; this technique would likely apply best to a batch treatment. In other embodiments, the ethanol solution 115 may be flowed sequentially through a plurality of pressure vessels 25, each having a pressure chamber 45 characterized by a different predetermined vacuum partial pressure and temperature to target one or more specific congeners 120.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

What is claimed is:

1. A method for rehabilitating alcohol, comprising:
   a) placing a quantity of ethanol solution in a pressure-controllable environment;
   b) decreasing the pressure of the pressure-controllable environment to about 25 Torr;
   c) holding the pressure of the pressure-controllable environment at about 25 Torr for a first predetermined period of time;
   d) removing ethyl acetate from the ethanol solution to yield a first treated ethanol solution;
   e) removing the first treated ethanol solution from the pressure-controllable environment;
   wherein steps a) through e) occur at ambient temperature; and
   wherein no distillation occurs during steps a) through e).

2. The method of claim 1, and further comprising:
   f) after b) and before e), cooling the pressure controllable environment.

3. The method of claim 2 wherein the pressure controllable environment is maintained at about 22 degrees Celsius.

4. The method of claim 1, wherein the predetermined period of time is about 5 seconds.

5. The method of claim 1, wherein the first treated ethanol solution has about one-half the ethyl acetate concentration of the ethanol solution.

6. The method of claim 1, wherein the first treated ethanol solution has about one-third the ethyl acetate concentration of the ethanol solution.

7. The method of claim 1, wherein the first treated ethanol solution is a mixture of water and a distillate fraction, and wherein the distillate fraction has a maximum ethyl acetate concentration of about 0.05 weight percent.

8. The method of claim 1, wherein the first treated ethanol solution is a mixture of water and a distillate fraction, and wherein the distillate fraction has a maximum ethyl acetate concentration of about 0.03 weight percent.

9. The method of claim 1, and further comprising:
   g) removing at least one non ethyl acetate congener from the ethanol solution.

10. The method of claim 1, and further comprising:
    h) removing at least one non ethyl acetate congener from the first treated solution to yield a second treated solution.

11. The method of claim 1 wherein the pressure controllable environment further comprises:
    a pressure vessel defining a pressure controllable chamber;
    a water jacket at least partially surrounding the pressure controllable chamber and in thermal communication therewith;
    a liquid inlet port in fluidic communication with the pressure controllable chamber;
    a gas outlet port in fluidic communication with the pressure controllable chamber;
    a vacuum pump in fluidic communication with the gas outlet port;
    a collection vessel;
    a liquid outlet port in fluidic communication with the pressure controllable chamber.

12. A method for removing unwanted congeners from an ethanol solution, comprising:
    a) establishing a partial vacuum in a pressure vessel;
    b) flowing a quantity of ethanol solution into the pressure vessel;
    c) at least partially preferentially removing at least one unwanted congener from the ethanol solution to yield a treated ethanol solution;
    d) extracting the treated ethanol solution from the pressure vessel;
    wherein while in the pressure vessel, the ethanol solution remains liquid';
    wherein the partial vacuum is about 25 Torr;
    wherein step c) is performed at about 22 degrees Celsius for about 5 seconds; and
    wherein during steps a)-d), no distillation occurs.

13. The method of claim 12, wherein the unwanted congener is ethyl acetate.

* * * * *